US009555207B2

(12) United States Patent
Eifler et al.

(10) Patent No.: US 9,555,207 B2
(45) Date of Patent: Jan. 31, 2017

(54) GEL FILLING FOR PATIENT INTERFACE AND METHOD FOR PRODUCING PATIENT INTERFACE WITH A GEL FILLING

(71) Applicants: Martin Eifler, Glueckstadt (DE); Martin Bechtel, Winsen/Luhe (DE); Arnold Frerichs, Buxtehude (DE); Matthias Pulla, Hamburg (DE); Henry Hahn, Hamburg (DE); Joachim Gardein, Canary Island (ES)

(72) Inventors: Martin Eifler, Glueckstadt (DE); Martin Bechtel, Winsen/Luhe (DE); Arnold Frerichs, Buxtehude (DE); Matthias Pulla, Hamburg (DE); Henry Hahn, Hamburg (DE); Joachim Gardein, Canary Island (ES)

(73) Assignee: LOEWENSTEIN MEDICAL TECHNOLOGY GMBH + CO. KG, Hamburg (DE)

( * ) Notice: Subject to any disclaimer, the term of this patent is extended or adjusted under 35 U.S.C. 154(b) by 713 days.

(21) Appl. No.: 13/968,580

(22) Filed: Aug. 16, 2013

(65) Prior Publication Data
US 2013/0340763 A1 Dec. 26, 2013

Related U.S. Application Data

(63) Continuation of application No. 12/455,678, filed on Jun. 4, 2009.

(30) Foreign Application Priority Data

Jun. 5, 2008 (DE) .................. 10 2008 026 906

(51) Int. Cl.
*A61M 16/06* (2006.01)

(52) U.S. Cl.
CPC ......... *A61M 16/06* (2013.01); *A61M 16/0622* (2014.02); *A61M 16/0633* (2014.02); *A61M 16/0666* (2013.01); *A61M 2210/0618* (2013.01)

(58) Field of Classification Search
CPC ...................................................... A61M 16/06
USPC ................... 128/206.24; 156/145, 325; 264/4
See application file for complete search history.

(56) References Cited

U.S. PATENT DOCUMENTS

| 3,715,047 A | * | 2/1973 | Sado | 215/261 |
| 3,852,832 A | * | 12/1974 | McGhan et al. | 623/8 |
| 3,942,423 A | * | 3/1976 | Herzfeld | 99/277.1 |
| 4,086,666 A | * | 5/1978 | Vaskys et al. | 623/7 |
| 4,455,691 A | * | 6/1984 | Van Aken Redinger et al. | 623/8 |

(Continued)

FOREIGN PATENT DOCUMENTS

WO 9709090 A1 3/1997

*Primary Examiner* — Daniel Lee
(74) *Attorney, Agent, or Firm* — Abel Law Group, LLP

(57) ABSTRACT

The invention concerns a gel covering of a patient interface. This gel covering has a mask connection area by which its side that faces away from the patient is joined with a mask body. The patient interface can be designed, for example, as a respiratory mask. On its side that faces the patient's face, the respiratory mask has thin, inwardly formed, peripheral contact lips. The respiratory mask has accessories that allow it to be fastened on the patient's head as well as a hose connection for supplying air. At least one region formed from a filler is placed in or on the walls of the gel covering. The method is used to produce the gel covering of the invention.

20 Claims, 20 Drawing Sheets

(56) References Cited

U.S. PATENT DOCUMENTS

| | | | |
|---|---|---|---|
| 5,370,688 A * | 12/1994 | Schulz et al. .................... 623/7 |
| 5,647,357 A | 7/1997 | Barnett et al. |
| 5,884,624 A | 3/1999 | Barnett et al. |
| 2005/0199239 A1 | 9/2005 | Lang et al. |
| 2007/0055371 A1 | 3/2007 | Laghi |

* cited by examiner

A-A

B-B  Fig. 8 a)
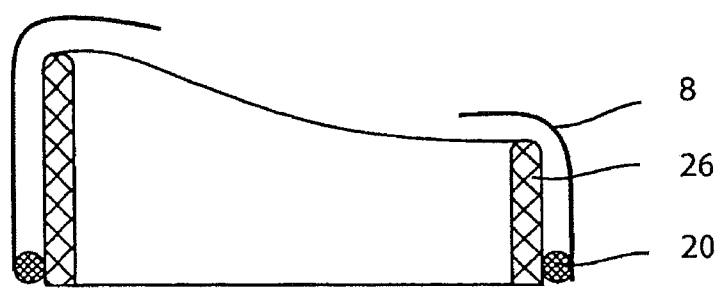
b)
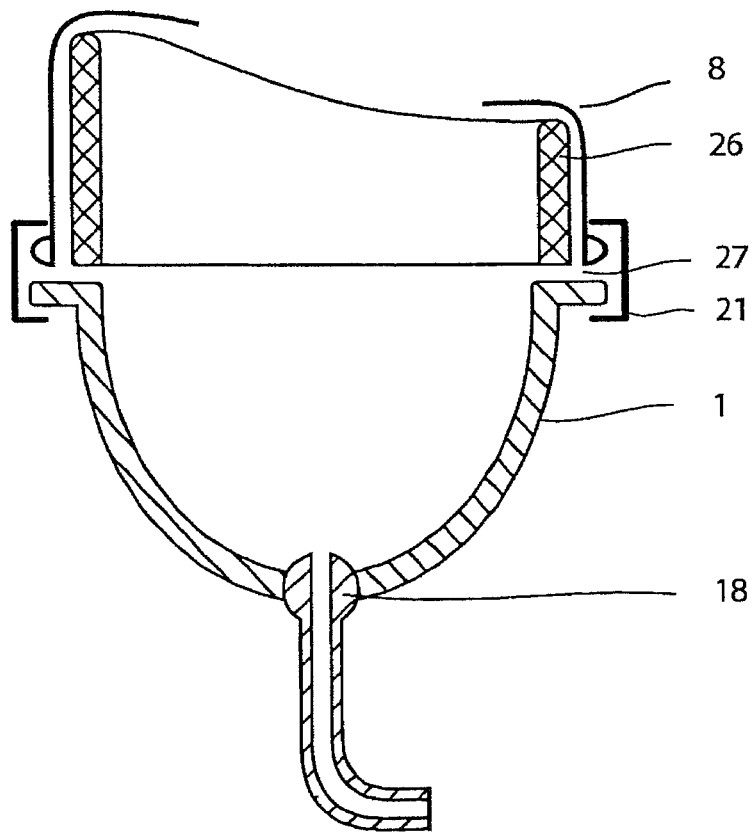
Fig. 11

GEL FILLING FOR PATIENT INTERFACE AND METHOD FOR PRODUCING PATIENT INTERFACE WITH A GEL FILLING

CROSS-REFERENCE TO RELATED APPLICATIONS

The present application is a continuation of U.S. patent application Ser. No. 12/455,678, filed Jun. 4, 2009, the entire disclosure of which is expressly incorporated by reference herein, which claims priority under 35 U.S.C. 119 of German patent application 10 2008 026 906.9, filed Jun. 5, 2008.

BACKGROUND OF THE INVENTION

1. Field of the Invention

The present invention relates to a method for producing a patient interface that contains a gel filling.

2. Background of the Invention

A prior-art gel rim for a ventilator mask, as described in EP 0 799 076 B1, is made of a polyurethane (PU) gel, which is enclosed in a protective PU foil. An additional silicone covering is positioned between the patient's face and the PU gel body. The wall thicknesses of the PU foil and the silicone covering are held essentially constant. The hardness of the gel filling here is in the range below 10 Shore 00.

The material properties and hardness properties are not equally well suited for all users. Polyurethanes (PU) are formed by a condensation and adduction reaction between isocyanates and polyols. Numerous additives are used in the production of PU. Polyurethanes that are not completely cured may contain residual monomers, for example, isocyanates. Exposure to isocyanates and additives can lead both to allergic and irritative contact eczemas. This causes some patients to reject the PU materials.

Therefore, the objective of the present invention is to improve the comfort of wearing a patient interface and thus to improve patient compliance. A further objective of the invention is a cost-effective method for producing the patient interface.

The stated objective is basically achieved with the characterizing features of Claim 1, wherein the gel covering has a cavity that is filled with a gel of a certain consistency and elasticity.

A further objective of the invention is to design a patient interface of the aforementioned type in such a way that wearing comfort is improved and cost-effective production is achieved.

This objective is basically achieved by the characterizing features of the associated dependent claims.

The gel filling can have a wide variety of characteristics. Possible fillings range from gel materials, such as polyurethane gel or silicone gel and the natural gel agarose, to foams, gas mixtures and liquids, such as saline solution, which is widely used in medicine. Ultimately, it may also be the same material of which the gel covering is made, especially when it is foamed. Due to the integrated design of the invention, the thickness of the walls of the gel covering can be adapted very precisely to specifications in order to lend greater or lesser stiffness to some sections of the gel covering, exactly as needed.

The invention is suitable for every patient interface that rests against the patient's body. The invention can thus be used especially in the following types of patient interfaces: nasal, oral, and full-face masks, in nasal pillows or nasal prongs, in emergency, home, and hospital ventilation, CPAP, APAP, and bilevel ventilation, and in medical orthoses and prostheses and support devices.

To produce the patient interface of the invention, it is proposed that the gel covering be produced with at least one cavity by shaping methods from an elastic plastic, preferably a silicone, and that this cavity then be filled with the given gel. The cavity preferably should be filled through an opening provided for this purpose, which preferably is not situated in areas of the gel covering that come into contact with the skin.

It is especially preferred that the cavity be filled by injection of the filler material, and the covering is preferably pierced in its relatively thicker areas. After the filling operation, especially when the cavity is filled with liquid or gaseous fillers, the one or more openings are tightly sealed, for example, with a stopper, by welding or by adhesive bonding. Especially gaseous fillers can be placed under pressure during this operation, so that the pressure level can affect and determine the properties of the gel body.

In an alternative method of production, a covering blank is first sealed by a stopper, and a permanent connection between the covering blank and the stopper is then produced by the use of joining means, with the sealed covering being produced from a uniform material, preferably silicone.

In an alternative method of production, the geometry of the covering blank is predetermined in the production process by at least one metal core, and after the covering blank has been produced, the metal core is removed through an opening in the covering blank, where the length of the opening is less than half the circumference of the covering blank.

In addition, it is proposed that a covering blank be produced which is open in the area that defines the place of contact between the body of the mask and the patient interface. In the next step, the covering blank can be adhesively bonded onto the interface of the patient interface. In this connection, the patient interface can consist of a hard plastic (preferably PC, PP, or PA), silicone, or a hard plastic (preferably PC or PA) with an integrally fabricated silicone border (double-shot molding). This solution offers economic advantages, since only one joining operation is carried out.

Furthermore, it is proposed that a covering blank be produced which is peripherally open. A sealed gel body is inserted into the covering blank and then sealed by adhesive bonding or vulcanizing.

In accordance with the invention, it is also proposed that a covering blank be produced with several openings. All of the opening but one are then sealed. The covering is filled with gel through the remaining opening, which is then sealed by a stopper.

The region of the gel-filled covering that constitutes the contact contour to the patient is preferably thinner than 5 mm in cross section, especially preferably thinner than 3 mm, and most preferably thinner than 2 mm. In this way, a relatively hard gel feels like a soft gel to the patient. At the same time, the gel-filled covering is very light due to the thinness of the walls.

Optionally, a second skin is placed over the gel-filled covering and is thus positioned between the gel-filled covering and the patient when the patient interface is being used. The second skin can be undetachably joined with the gel body (formed as an integral part or adhesively bonded). Alternatively, the second skin can be mounted as a separate member on the gel body or on the patient interface.

The wall of the filled covering and/or the wall of the second skin preferably has a thickness, at least in some areas, of about 0.5 mm and, alternatively, even only 0.3 mm. In some sections, the thickness is up to 1 mm.

The gel body is secured on the patient interface by a frame, for example, by means of a clip mechanism.

Alternatively, the gel body is adhesively bonded onto the patient interface. The open gel body is preferably bonded directly onto a hard plastic part (PC) of the patient interface. Alternatively, the patient interface is fabricated by double shot technology and has a silicone component in the area of the interface with the gel body. The gel body is joined with the patient interface in this area by direct joining of the two silicone parts.

It should be noted that the scope of the present invention is not limited solely to the preferred embodiments that have been presented, and more extensive combinations and variants of the present invention can be derived from the independent and dependent claims by an individual with average skill in the art without his having to leave the scope of the present invention.

BRIEF DESCRIPTION OF THE DRAWINGS

Details of the present invention will now be described on the basis of the specific embodiments illustrated in the accompanying drawings, in which functionally equivalent parts are referred to with corresponding reference numbers.

In the drawings:

FIG. 11 shows a cross section through the gel covering and the patient interface with a second cover.

FIG. 1 shows a patient interface in the form of a nasal mask, whose mask body 1 is made of a relatively strong material and which has a gel-filled covering 3. This covering 3 is the part of the mask that rests on a patient's face (not shown) and provides the necessary seal. The mask body 1 is connected by an angled connector 2 to a sleeve 4, which is rotatably supported and serves to connect the mask to a respiratory gas hose (not shown). To guarantee secure positioning of the respiratory mask on a patient's head, a forehead support 5 is used, which has a shaft 35 that is inserted in a mount 36 of the mask body 1. The connector 2 and the mask body 1 are connected by a ball-and-socket joint 18. The ball-and-socket joint 18 is supported by a retaining ring 31. A forehead pad 13 is fastened on a mount 12 of the forehead support in a way that allows it to slide. The forehead pad 13 provides additional support for the mask on the forehead of the patient. The mask is fastened on the patient's head with straps (not shown).

Figure 1:
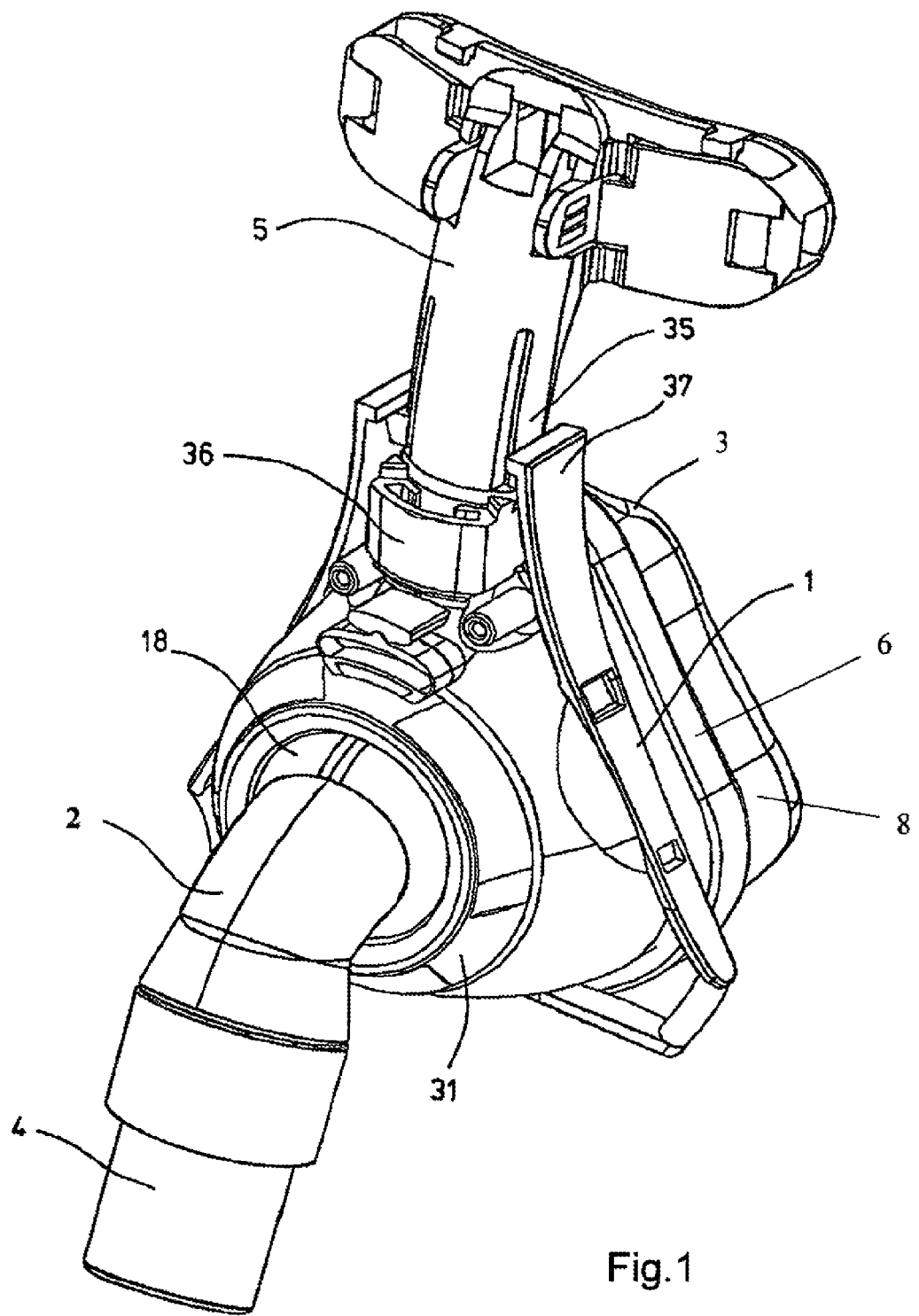
FIG. 1 shows a perspective view of a patient interface in the form of a nasal mask.

On its contact side intended for contact with the patient's face, the gel covering 3 ends in a contact lip 7 that becomes thinner and thinner and provides the gel covering 3 with a soft and flexible contact zone all around its edge. The walls of the gel covering 3 are terminated on the patient interface side with a connecting member 6, which is realized either as a single piece with the gel covering 3 and consists of the same material as the gel covering 3 or as a part that is to be attached by an adhesive or welded joint.

The connecting member 6 is mechanically joined with a base part (not shown) of the mask by means of catching parts, or, alternatively, it can be undetachably joined with the base part of the mask by adhesive bonding or welding. The cavity 9 is bounded by the outer skin 8.

In accordance with the invention, the thickness or depth of the filler 15 can also be essentially constant along the cross section of the gel covering 3.

To fill the cavity 9 with a filler 15, the gel covering 3 has at least one opening, which is not shown in FIG. 1. This opening can be positioned in any desired place in the wall of the gel covering 3 except in the vicinity of the outer surfaces of the contact lips 7 and their surrounding area to prevent it from having a disturbing effect on the facial skin that will be contacted there. The filling hole is preferably sealed by adhesive bonding, welding or plugging with a stopper.

By using a thin filling of the cavity 9, for example, a soft buffer zone is realized. The buffer zone 16 is provided with a supporting function if the cavity 9 is filled with relatively inflexible material, for example, with gel with a hardness above 15 Shore 00. The flexible buffer zone 16 can also be realized in such a way that the filling has two different elastic properties at least in certain areas.

Figure 2:
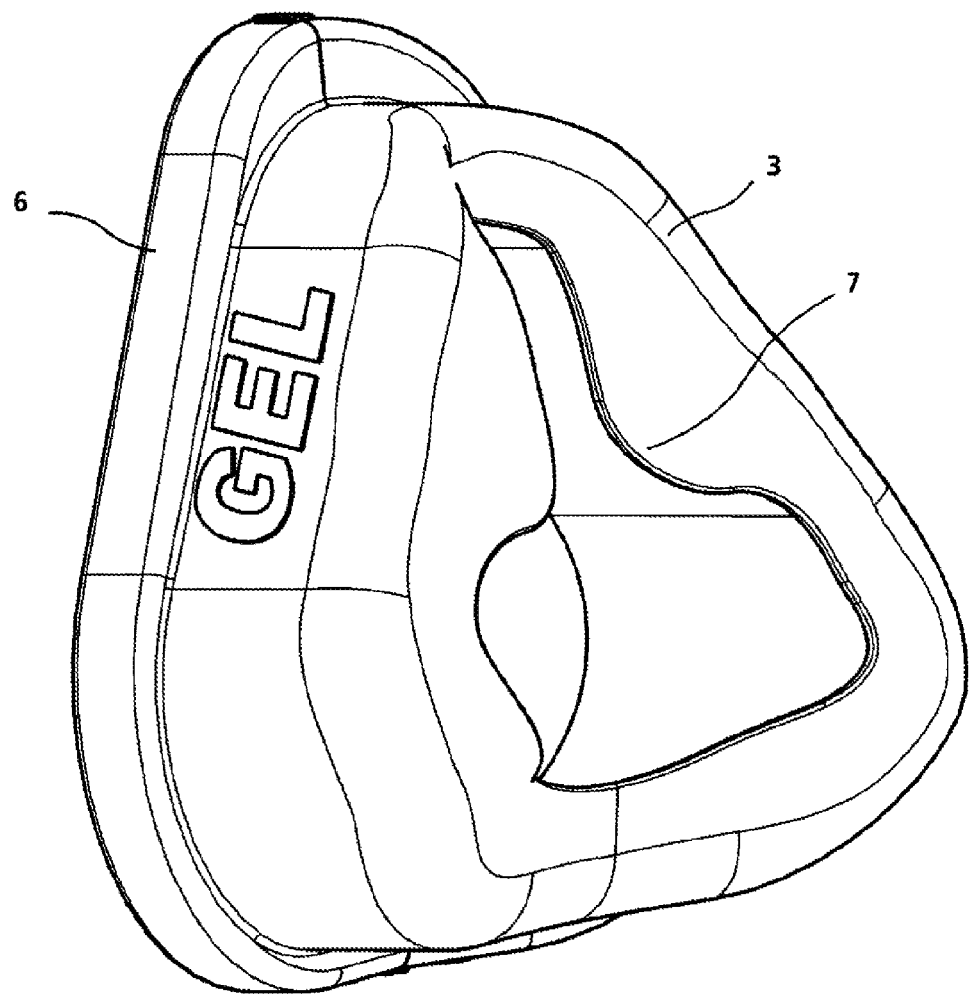
FIG. 2 shows a perspective view of an embodiment of the gel covering.

FIG. 2 is a perspective view of a gel covering 3, which has contact lips 7 all around its edge, which are designed to be formed inwardly into the gel covering 3. The wall 6 of the gel covering 3 serves to connect it with the mask body (not shown here) by means of mechanically locking elements, and it contains at least one cavity 9 with a filler 26, which is not shown in the drawing.

Figure 3:
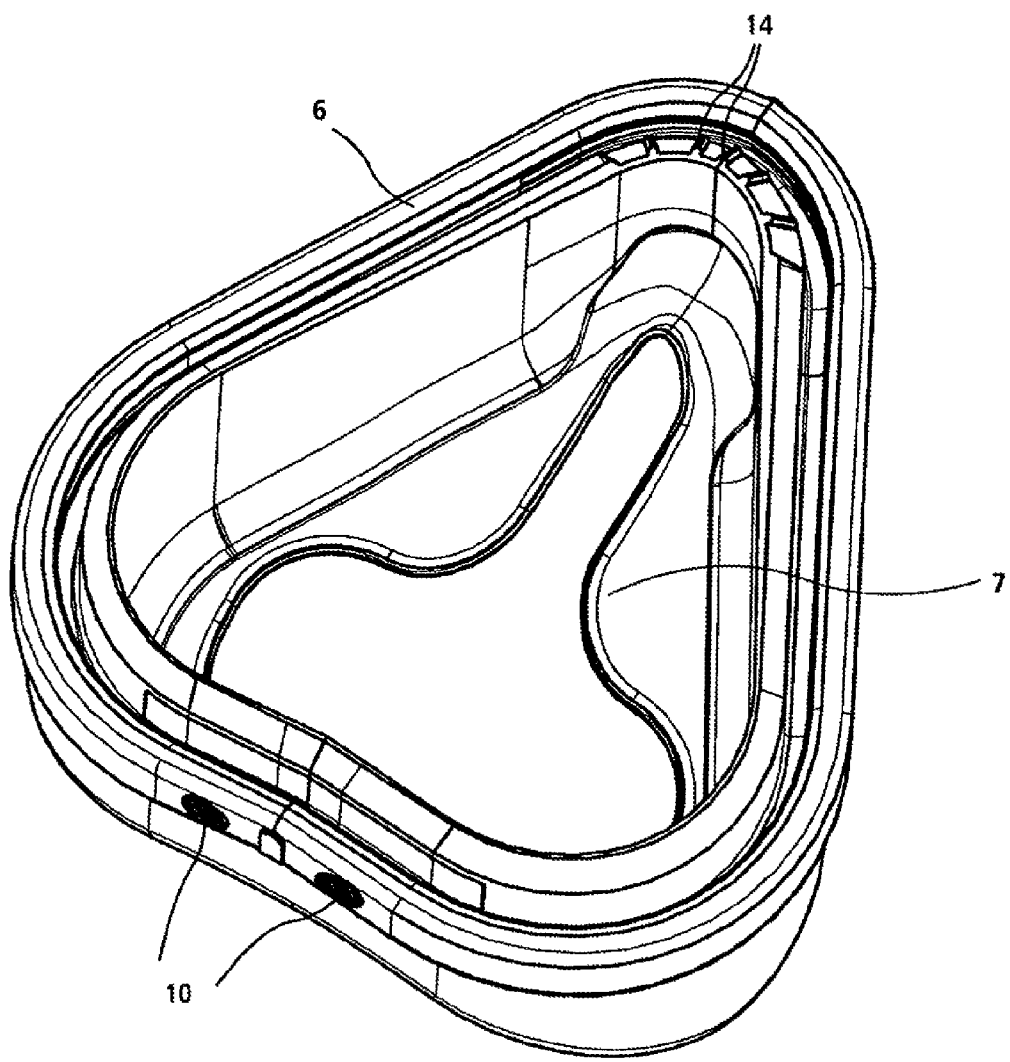
FIG. 3 shows the embodiment of the gel covering in FIG. 2 from below.
Figure 4:
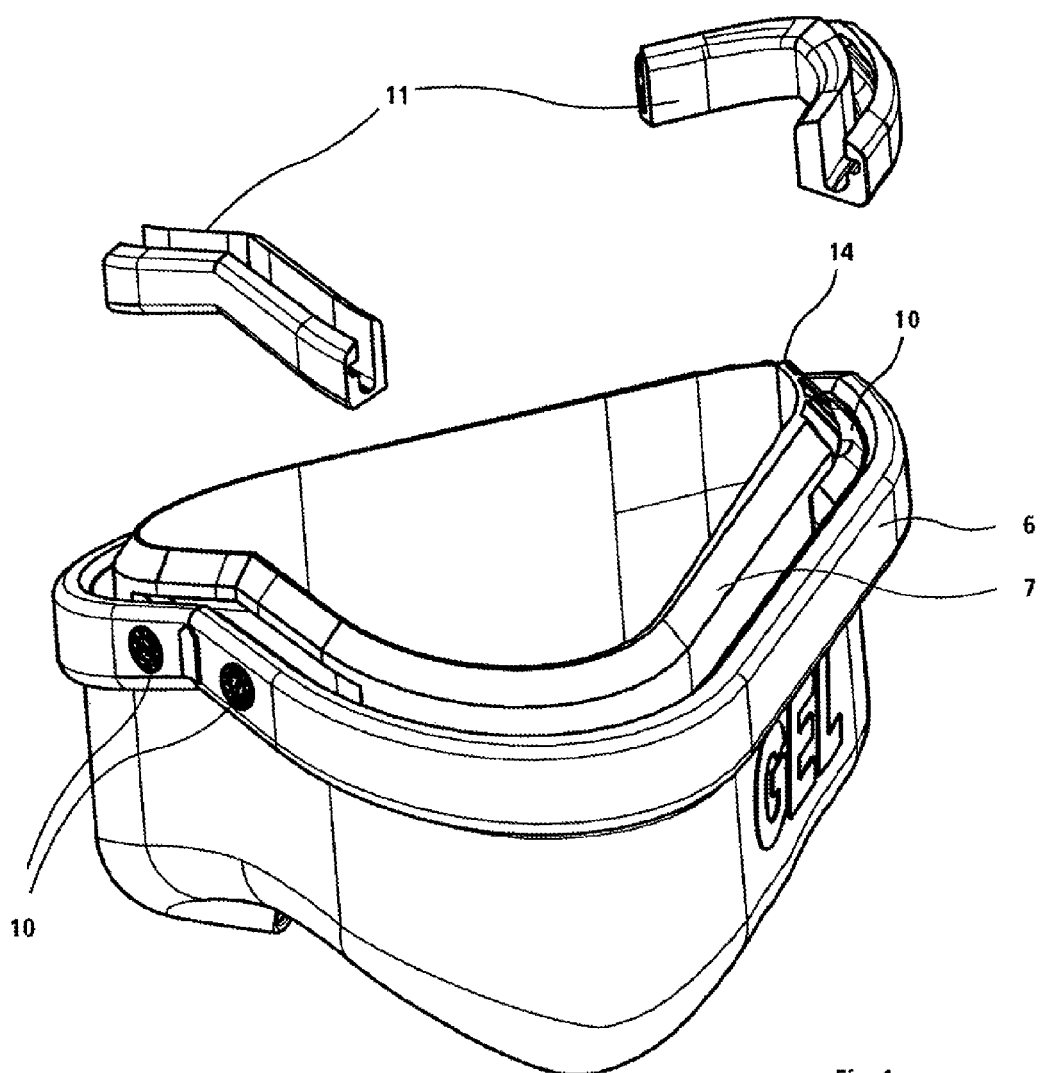
FIG. 4 shows a side view of the embodiment of the gel covering in FIG. 2, FIGS. 5 to 8 each show a cross section through the gel covering.

FIGS. 3 and 4 show further perspective views of the mask part according to FIG. 2. FIG. 3 reveals openings 10 located in the area of the lower part of the mask. The cavity 9 is filled with the gel through these holes. In one embodiment, the openings 10 are realized as hollows in the outer skin 8, which are sealed with stoppers 11 after the filling operation. In another embodiment, the openings 10 are realized as thickened regions of the outer skin, which are pierced with an injection needle to fill the cavity 9 and which seal themselves due to the elasticity of the material when the needle is pulled out. Ribs 14 are formed in the connecting member 6, which serve a position coding function and determine the orientation. In addition, the ribs allow a pneumatic passage from the interior space of the mask to the pressure gage socket (not shown) of the mask body.

FIG. 4 illustrates especially the use of stoppers 11, which are inserted in the openings 10 of the gel covering 3 after the cavity has been filled with the gel. The fabrication principle will be explained in greater detail later. The openings are preferably formed in the area of the connecting member 6, since the material thickness is greater there. A greater material thickness of the outer skin 8 is to be preferred both for the injection and for the subsequent adhesive bonding of the stopper 11 in the opening 10. The material thickness of the outer skin 8 in the area of the opening 10 is preferably greater than 1 mm in cross section and especially preferably greater than 2 mm in cross section. The opening 10 in the upper right section of the drawing is formed as part of the connecting member 6. Accordingly, the corresponding stopper 11 has the profile of the connecting member 6. The cross section of the stopper 11 reveals a peripheral undercut, which receives a corresponding groove in the mask body. The connecting member 6 has a slightly elevated and beveled insertion aid 17, which helps to achieve simple mounting of the gel rim on the mask body.

Figure 5:
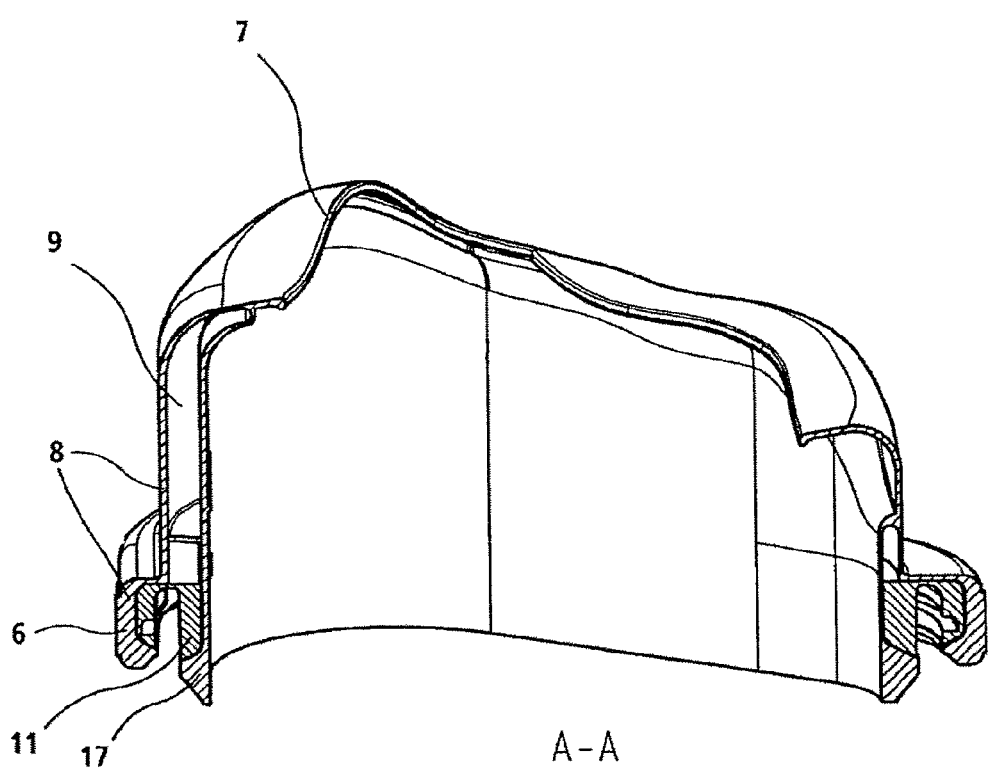
Figure 6:
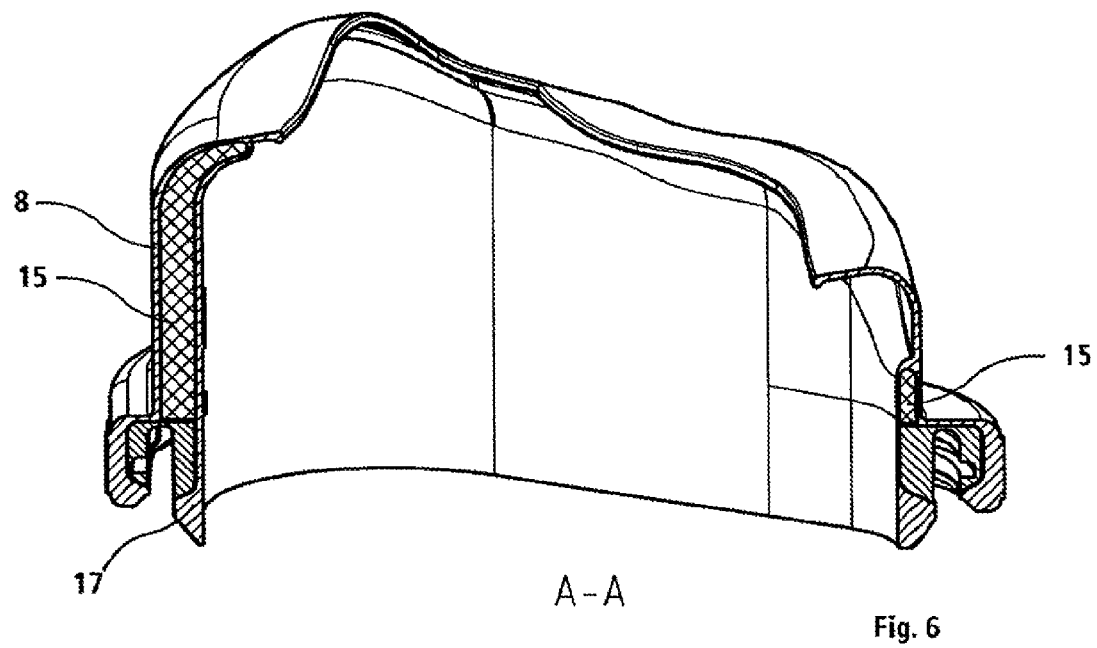
Figure 7:
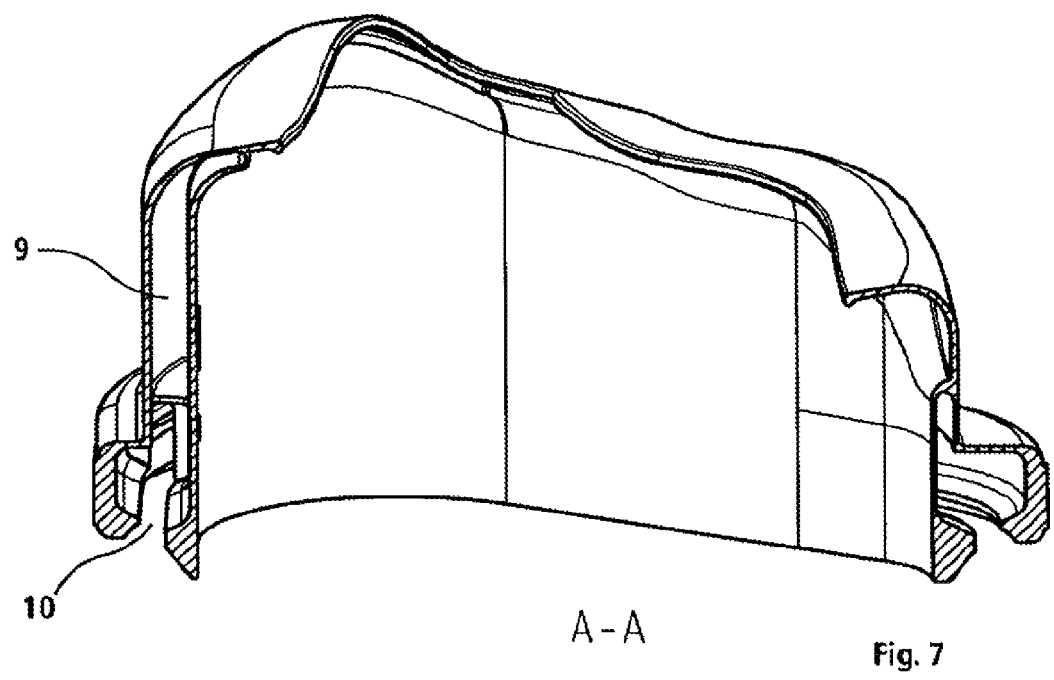
Figure 8:
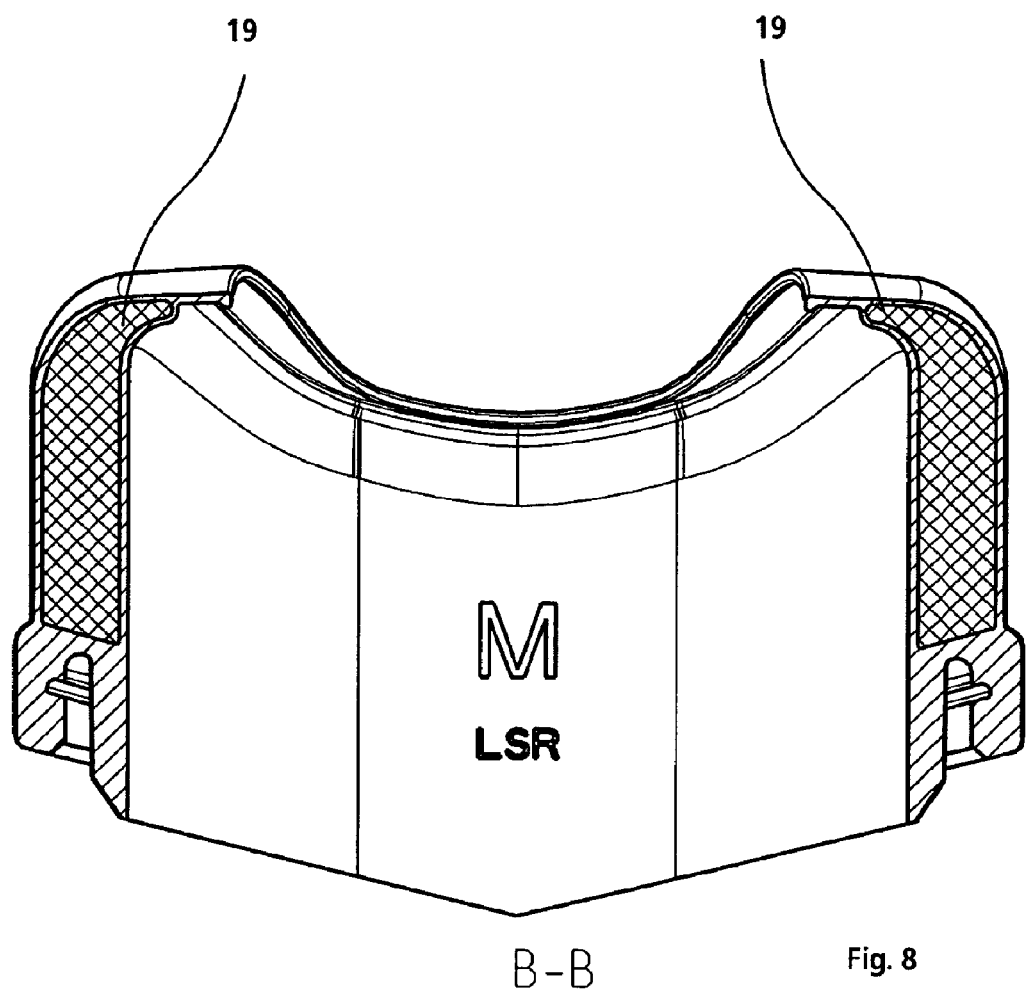

FIGS. 5 to 8 show cross sections through cavities filled with filler 15. In FIG. 5, the openings 10 are sealed with stoppers 11, and the cavity 9 is filled with gas. The drawing shows that the material thickness in the area of the connecting member 6 is at least twice as great in some sections as the material thickness in the area of the outer skin 8. In FIGS. 6 and 8, the cavity is homogeneously filled with a filler 15. FIG. 7 shows the openings 10 without stoppers and the cavities 9 without a filling. FIG. 8 additionally shows that the cavity filled with filler 15 can be shaped in various ways. In addition, in cross section, the cavity filled with filler 15 shows its thinnest point 19 in the area of contact with the patient.

The filler 15 in accordance with the invention makes it possible, within a very large range of shaping possibilities, to provide the gel covering 3 with predeterminable increased stability exactly in those areas in which it is needed, while other areas of the gel covering 3 are left with a thin wall thickness and/or a very soft material consistency.

The filling opening repeatedly described above can be designed as an opening in the conventional sense, which is resealed after the filler 15 has been applied. In particular, however, it is also possible to introduce the filler 15 in a flowable consistency by injection into the cavity 9. If this injection of the filler is carried out in a thick-walled region in a covering 8, 11 of the cavity, then, after the injection device has been withdrawn, the injection channel automatically seals itself due to the elastic properties of the material. This greatly facilitates the manufacturing process.

In another embodiment, different material thicknesses of the walls 8, 11 of the gel covering 3 can be chosen, so that, on the one hand, the thickness guarantees the necessary stiffness and, on the other hand, guarantees contact with the skin that is as soft and as tightly sealing as possible.

Especially in the area of the walls of the gel covering 3 that rest against the face, the wall has a smaller material thickness than the areas of the walls of the gel covering 3 that do not rest on any parts of the face 6.

The material thicknesses are preferably low in the area of the walls of the gel covering 3 that rest on the bridge of the nose. It is especially preferred that the material thickness of the wall in the area that rests on the bridge of the nose is less than in those areas of the wall of the gel covering 3 that rest on other parts of the face. This results in an optimal sealing function with minimal application of pressure in the area of the sensitive bridge of the nose.

Figure 9:
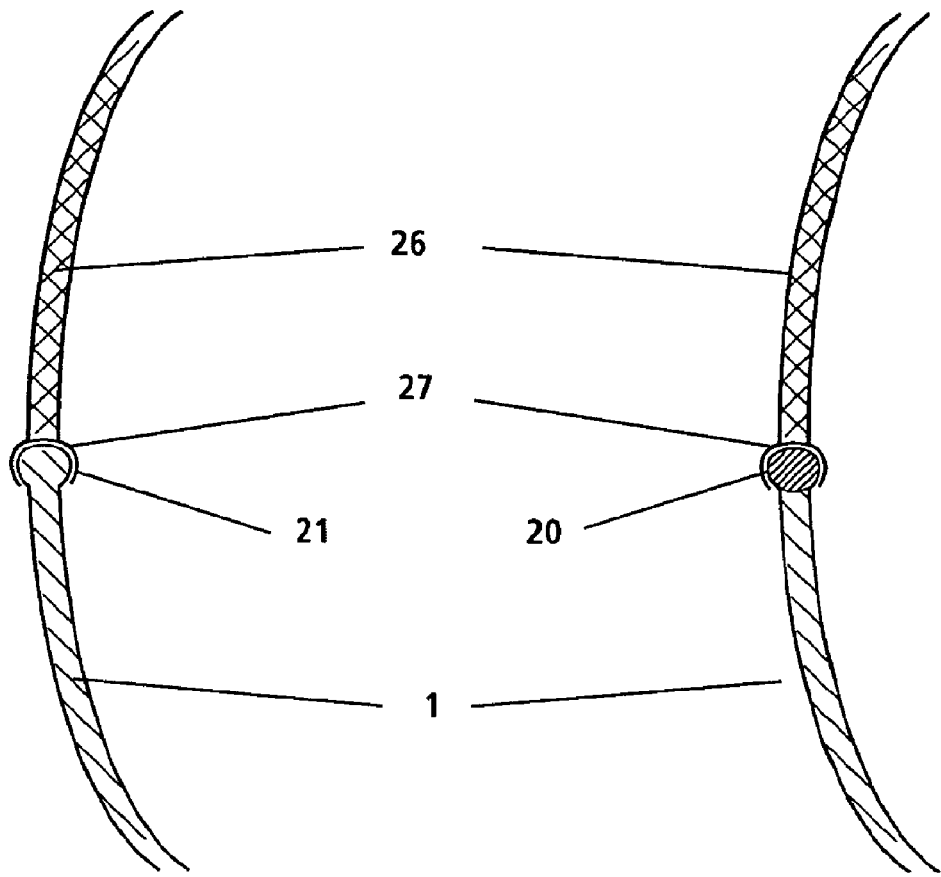
FIG. 9 shows a cross section through the gel covering and the patient interface in the contact area.

FIG. 9 illustrates connections between the gel body 26 and a connecting member of the patient interface. The connecting member can consist of polycarbonate. The joint can be realized by a positive-locking connection according to the drawing on the left in FIG. 9, while in the embodiment illustrated on the right, an adhesive bond can also be realized, even with the use of silicone.

Figure 10:
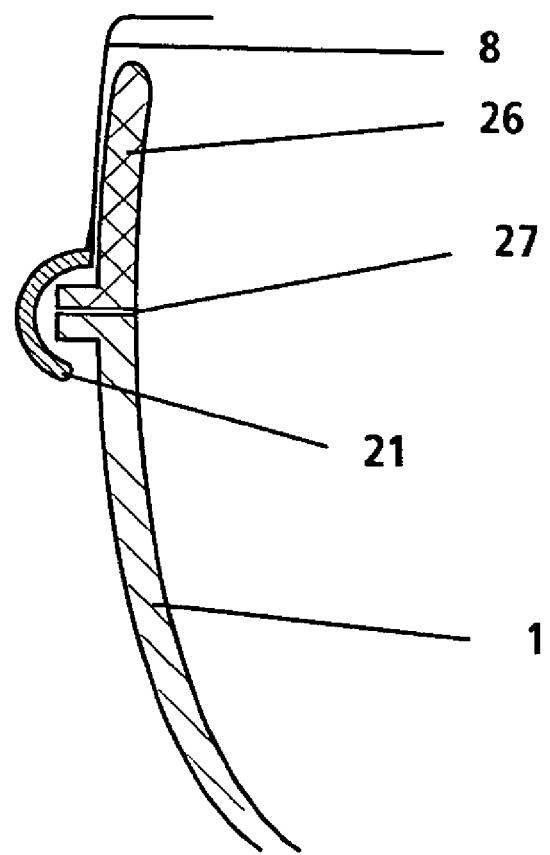
FIG. 10 shows a cross section through the gel covering and the patient interface in the contact area with mechanical locking.

FIGS. 10 and 11 show an embodiment of the gel covering 3 of the invention. In this case, the gel covering 3 is joined with the patient interface (mask body) by means of locking mechanical elements in a mask connection area. The mechanical locking element is designed here as part of the outer skin 8 of the gel body, for example, by the double-shot process, and it has a latch that encloses an undercut of the patient interface. In the area of the joint 27 between the gel body 26 and the patient interface, there is a sealing contour (not shown).

FIG. 11 shows that the outer skin 8 is adhesively bonded with the gel body. The outer skin is preferably formed as a thin silicone lip, which overlaps the contact zone of the gel body with the skin. The adhesive joint 20 is located in the area of the connecting member 6. In addition, a locking mechanism that detachably connects the gel body 26 with the body of the patient interface can be realized in the area of the connecting member 6.

Figure 12:
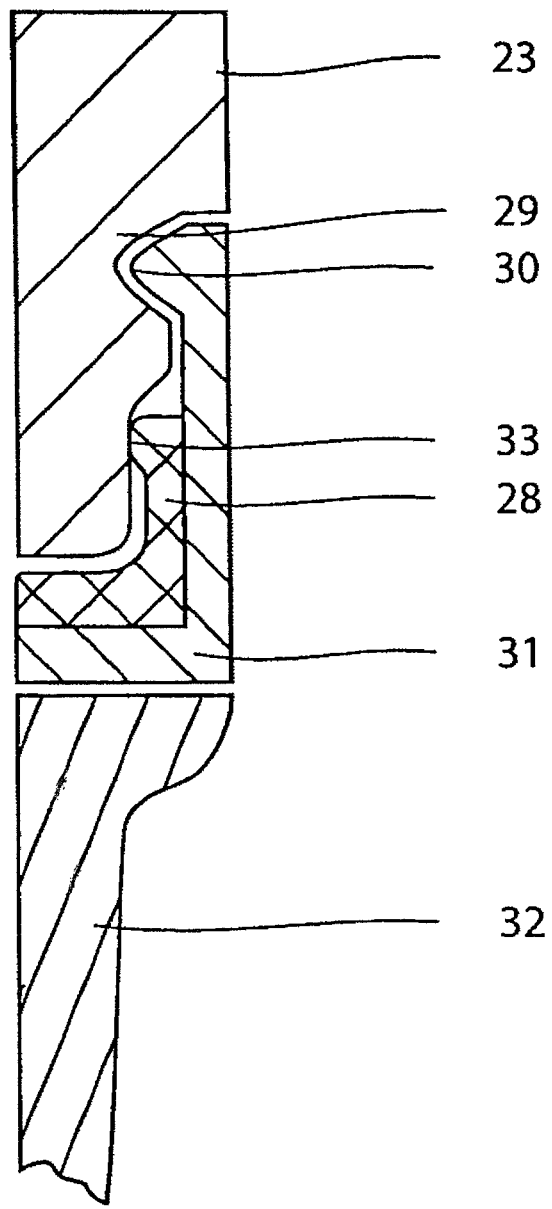
FIG. 12 shows a cross section through the gel covering and the patient interface in the contact area with a sealing element.

FIG. 12 shows a cross section through the joint 27 between the gel body 26 and the connecting member of the patient interface 23. The connecting member of the patient interface 23 can consist of polycarbonate (PC) or PA and is preferably hard. The connection is made here with a snap connection, which can be realized peripherally or only in segments. In the case of nasal masks and full-face masks, a segmented snap connection in the area of the corners of the triangular mask body is preferably contemplated. A recess 29 in the area of the connecting member of the patient interface 23 serves to receive the corresponding snap hook 30. The snap hook frame 31 is injection-molded or adhesively bonded as a hard part peripherally or in segments onto the mask rim 3, 7, 8, 24, 25, 32 (silicone/PU). A sealing element that has at least one sealing contour 33 is located in the joint 27. The sealing element runs peripherally along the joint 27 and preferably provides a sealing effect in the radial direction.

Figure 13:
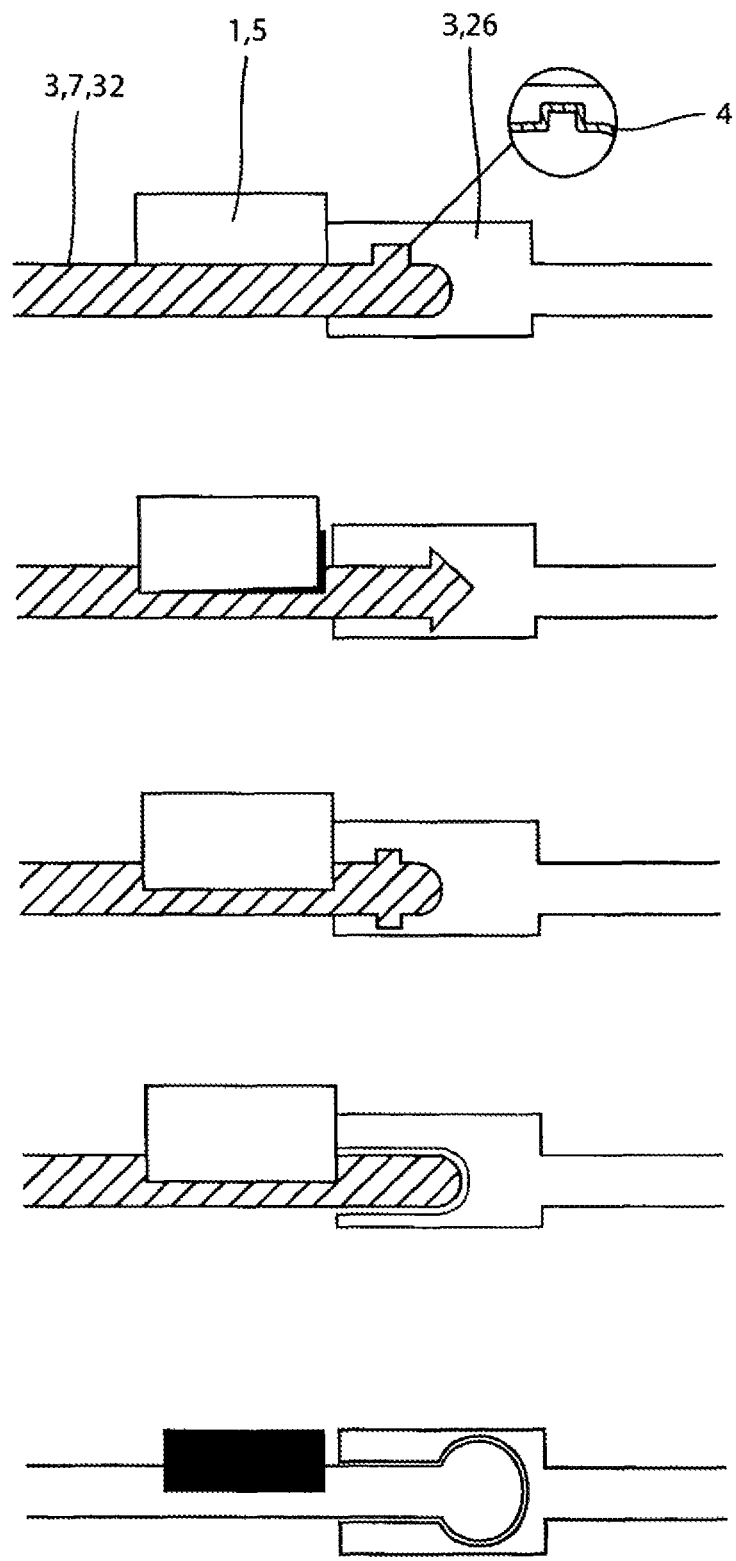
FIG. 13 shows five variants of possible means of connection.

FIG. 13 shows five variants of possible means of connection. The upper three variants in the figure have positive-locking connections between the silicone and the rim of the mask. The fourth embodiment shows adhesive bonding without positive locking. The bonding gap is at least partially filled with adhesive in this case. The fifth embodiment is again a positive-locking connection. Even in the positive-locking connections, additional connection by adhesive bonding is also possible in order to increase the strength of the connection. The strength of the connection can be increased still further if the frame element and the gel rim are also adhesively bonded.

Figure 14:
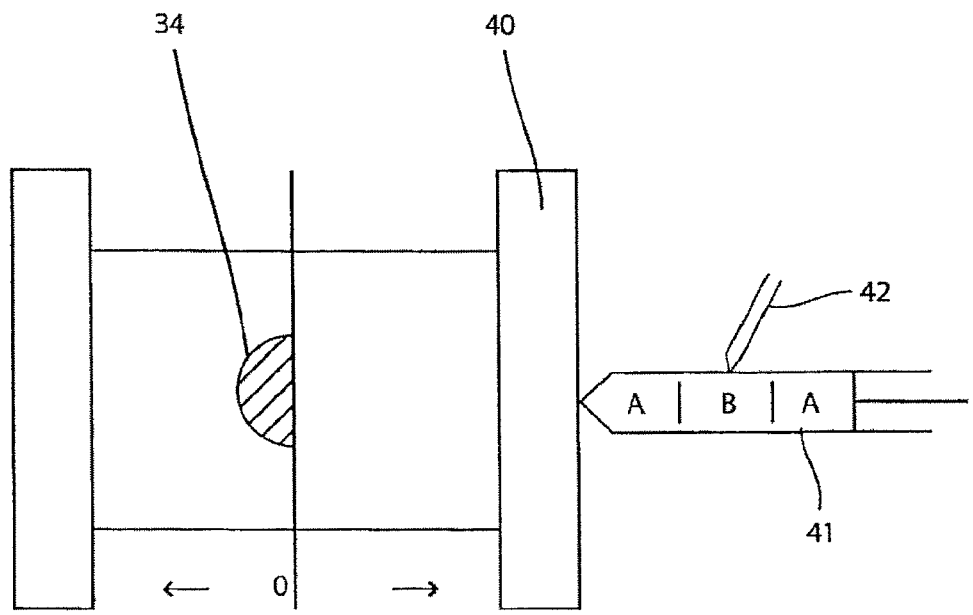
FIG. 14 is a schematic representation of injection molding with several components.

The gel rim and the gel are produced in a mold 34 of an injection molding machine 40; as shown in FIG. 14. To this end, the outer skin 8 (A) (e.g., silicone or TPE) is first injected and becomes deposited on the mold to form the outer skin. The gel (B) is then injected in the same or a second injection unit 41 and fills the entire interior space. It is also conceivable for the gel to first be produced from its two or more components at the time of the injection. For this purpose, at least one component is contained in a reservoir 41. This component is first metered in during or just before the injection of the gel fraction (B). If necessary, the first component is injected again to seal the injection point. This component is injected by the first injection unit or by a third injection unit.

The gel pad according to FIG. 14 is produced with an injection molding unit. To this end, the injection unit is filled in one shot with the first and the second component or the first component again (monosandwich).

It is also possible to inject a harder material as a third or additional component in order, if necessary, to realize a functional element or additional functional elements of the gel rim.

Figure 15:
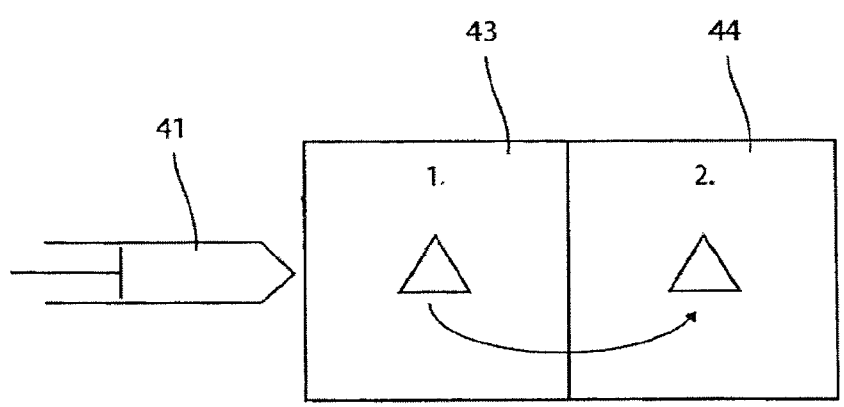
FIG. 15 is a sketch illustrating a production process.

The gel pad according to FIG. 15 is produced with an injection molding unit 41. In this case, the covering blank is transported from a first mold 43 to a second mold 44, where the filling with gel substance is carried out. In this operation, a part of the mold or the whole mold is transferred, together with the article so far produced, from one machine to the other. It is also possible to move only the article between the machines.

Figure 16:
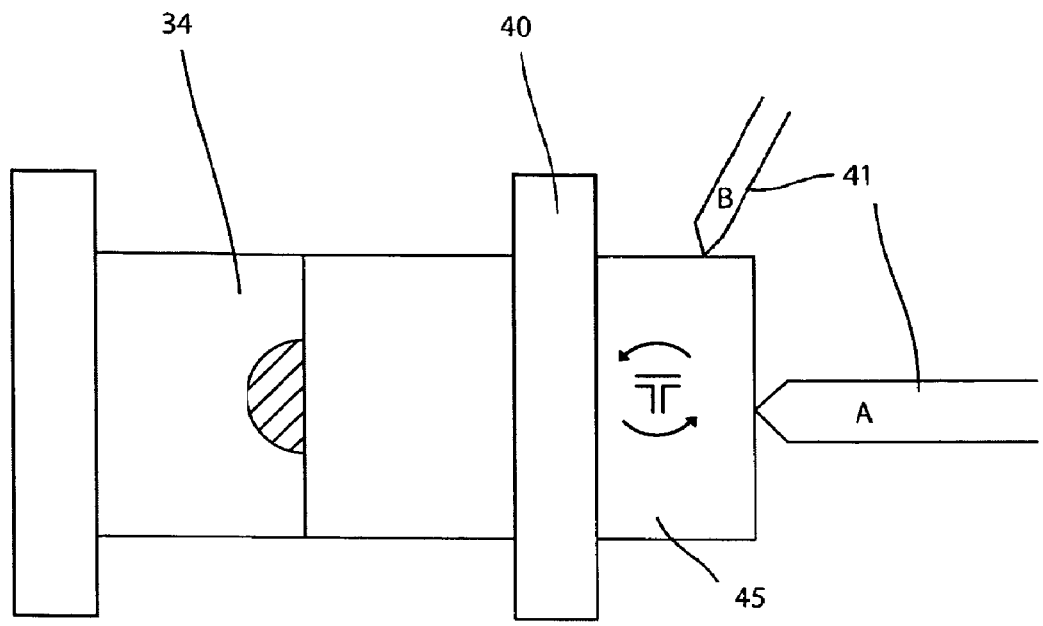
FIG. 16 shows a injection molding process with the use of a transfer plate.

However, as shown in FIG. 16, the filling can also be carried out with two, three or more injection units in one machine 40. The units are controlled by the machine and possibly by an additional transfer plate 45. the transfer plate switches from one component (a) to the next (B).

Figure 17:
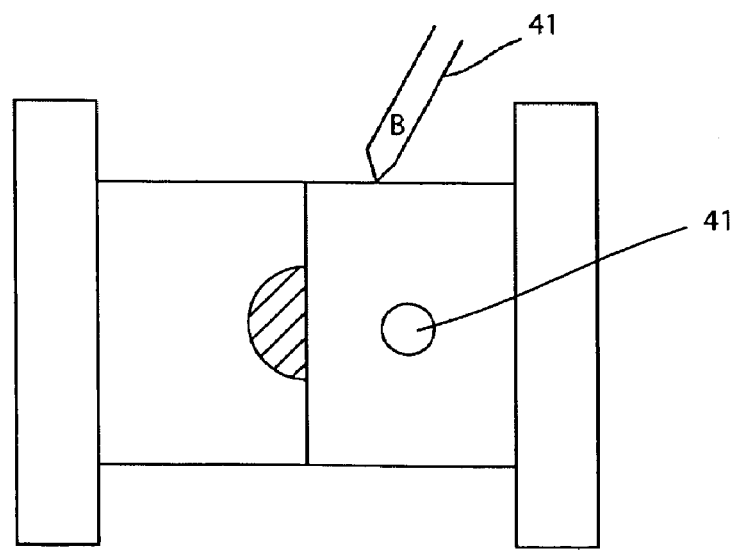
FIG. 17 is another drawing that illustrates the injection molding process.

It is also possible, as shown in FIG. 17, to carry out the production process with the use of a machine 40 with an integrated transfer plate 45. In this case, feeding from the various units 41 is controlled in the machine.

The injection operation can be optimized by a pressure buildup with an auxiliary medium between the first and second component. To this end, more material of the first component than is needed is injected into the mold. In an intermediate step, excess material is then forced back out of the mold by the auxiliary medium. Suitable auxiliary media for this purpose are gases as well as liquids.

The gel rim is produced quasi in one operation, in which the so-called monosandwich process is used. In the monosandwich process, two melts are first stratified one after the other in a common worm cylinder, such that the second melt is plasticated by a secondary extruder into the worm cylinder of the main machine. The injection operation is then carried out with only a single stroke, as in conventional injection molding. The sandwich structures result from the flow properties of the axially stratified melts in the worm cylinder.

The material that is injected first is deposited as a skin on the mold wall, and the material which follows forms the core. Thus, with respect to the gel rim, first the silicone skin (outer skin) is formed and then the silicone gel (core layer).

The prefabricated gel rim is manually or mechanically mounted on the frame geometry (double shot frame with a bubble and coupling for the central element), and the joint is adhesively bonded and/or vulcanized.

In this regard, it is contemplated that a projection of silicone 3.0-15.0 mm long is formed beyond the frame (on the patient side), which as a male or female joining unit fits the female or male matching part of the gel mask rim.

Before, during or after the mounting of the gel mask rim, this joint is filled either with a silicone adhesive or with an LSR (liquid silicone rubber). The silicone adhesive is cured under room conditions, while the LSR adhesive joint would be vulcanized under elevated pressure and temperature by means of an additional compression mold.

Figure 18:
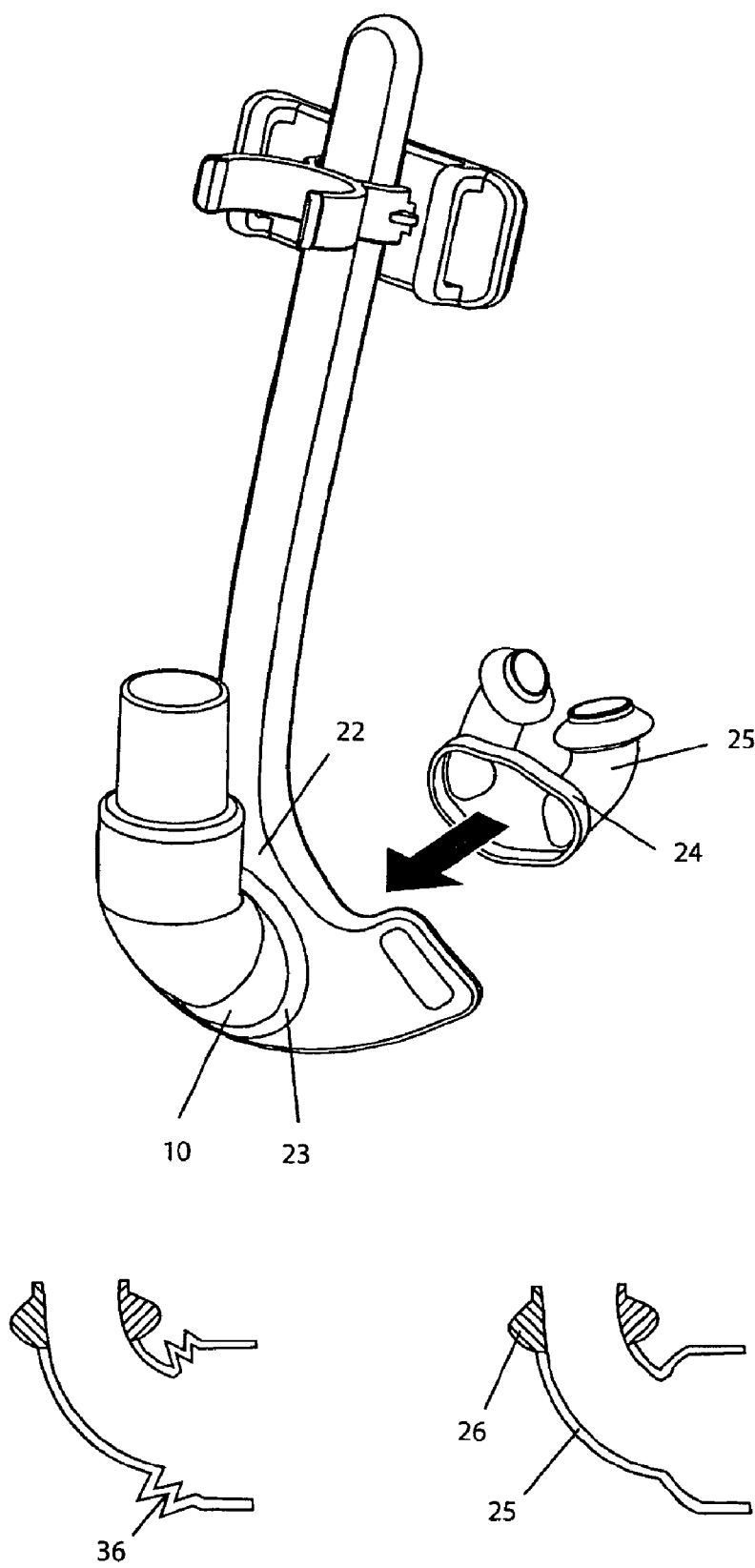
FIG. 18 shows a perspective view and two sectional views of a nasal pillow.

The nasal pillow mask is a special form of a patient interface and serves to convey gas to the patient's nose. As FIG. 18 shows, the pillows are produced from a soft material, such as silicone, which can be adapted to the shape of the nose, thereby providing a good seal and avoiding leaks. The shape of the pillows is oval or kidney-shaped. The two pillows form a unit. They can provide a seal directly on the edge of the nose or can be slightly inserted into the nose. Gel pads 26 embedded in the nasal pillows 25 can also prevent pressure points that might otherwise develop here. Small accordion folds 36 in the joining area of the nasal pillows allow better positioning of the nasal pillows 25 on the patient's nose.

The nasal pillows 25 are joined to the body 22 of the mask by a holding area made of a harder material. This can be joined with the nasal pillows by the double shot process and is held on the body 22 by a locking mechanism. Another variant provides direct joining of the soft nasal pillows 25 to the body 22. In this connection, the nasal pillow 25 is folded over the body 22 and held in the holding area 24 of the body 22. This holding area 24 can be formed in such a way that it forms the end support of the ball-and-socket joint 10.

In another embodiment, the ball of the ball-and-socket joint 10 can be inserted from the outside into the holding area 23 of the body 22 by the application of a small amount of force. To this end, it is provided that the ball or the socket is made of a stable plastic material, which readily elastically yields and deforms under the pressure of insertion of the ball but then returns to its original shape and holds the ball.

Figure 19:
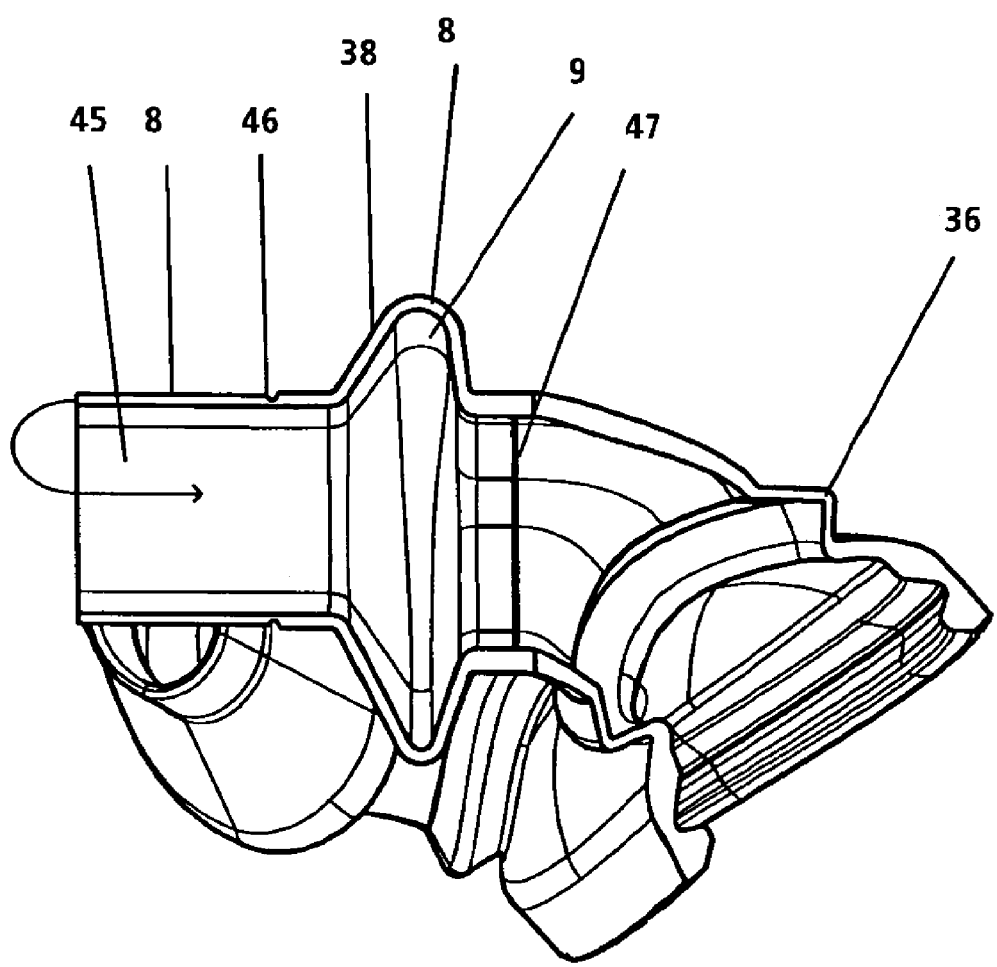
FIG. 19 shows a side view of and a longitudinal section through a nasal pillow.

FIG. 19 shows a side view of and a longitudinal section through a nasal pillow. To bound the cavity 9 for receiving the gel filling, the component of the extension 45 of the nasal pillow cushion 38 that extends to the left is produced, and after it has been released from the mold, this extension 45 is folded over towards the inside. This bounds the inside of the cavity, and the gel filling is shielded from the interior space. The extension 45 that has been folded over can be adhesively bonded with the other wall material. A bending point, which in the present case takes the form of a notch, is provided in the area of the extension 45. This makes it easier to fold over the extension and provides the length of the extension 45 to be folded over. In its folded state, the extension reaches as far as the stop 47.

Figure 20:
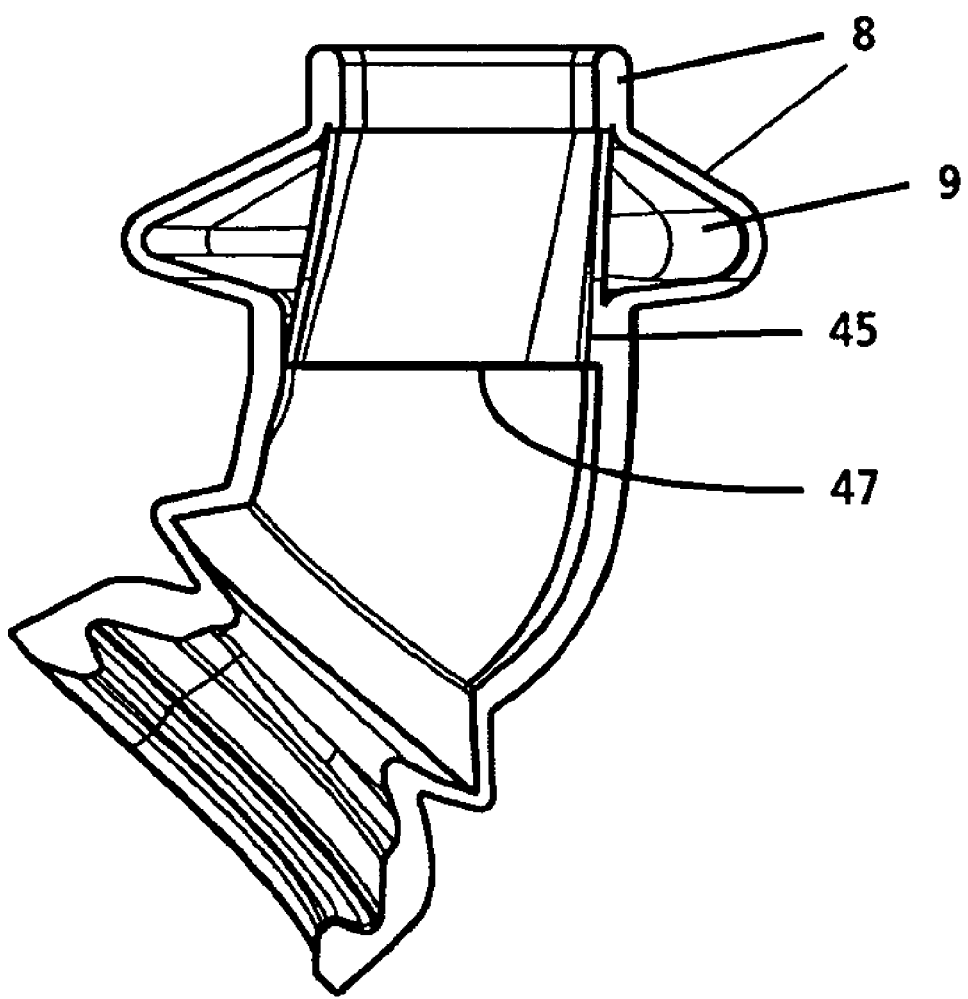
FIG. 20 shows an embodiment of a nasal pillow from FIG. 19.

FIG. 20 shows a side view of and a longitudinal section through a nasal pillow with the extension folded over. The cavity 9 for receiving the gel filling is bounded here on the gas-carrying inside by the extension 45 and on the outside by the outer skin 8. To this end, the extension 45 was folded over as far as the stop 47 and adhesively bonded. It is seen that the wall thickness of the outer skin 8 is lesser in the area of the nasal pillow cushion 38 that holds the gel filling than in the area that lies below the stop 47. The lesser wall thickness supports the pressure-relieving and sealing function of the gel filling.

Figure 21:
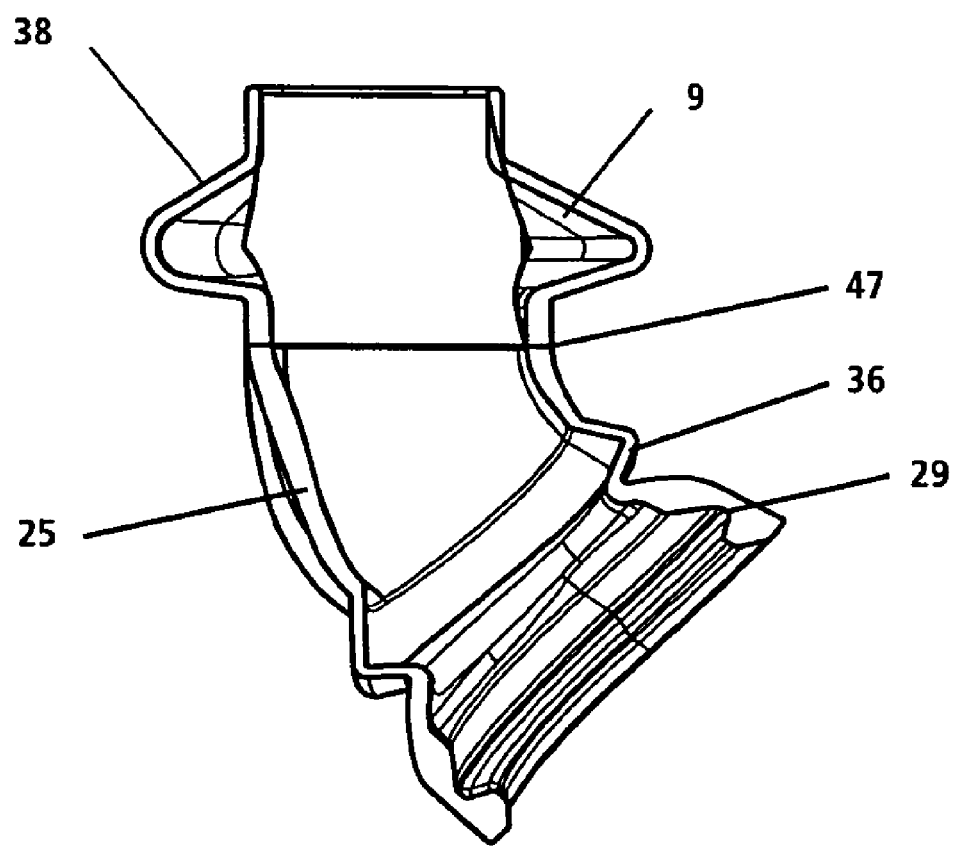
FIG. 21 shows an embodiment of a two-part nasal pillow.

FIG. 21 shows a side view of and a longitudinal section through a nasal pillow that consists of two parts. The body 25 of the nasal pillow and the nasal pillow cushion 38 are produced separately, and the nasal pillow cushion 38 is filled with the gel before it is joined with the body 25 by adhesive bonding.

Naturally, all of the geometries are conceivable/realizable in mirror-image arrangement (as an example, the groove in the silicone shoulder of the frame and the plug in the gel mask rim).

It is also possible for the geometry to be such that, e.g., the female end is preformed in such a way that it does not deform into its final position until it is mounted on the opposing end (male part). This effect would promote secure support and satisfactory adhesive bonding.

The embedding of gel fillings is accomplished by filling sections of the nasal pillow. This makes it possible to realize better wearing comfort and/or better strength. The material of the nasal pillows is usually silicone. The embedded gel is a silicone gel, which is realized with a hardness in the range of less than 20 Shore 00, preferably with a hardness in the range of 10-20 Shore 00, and more preferably with a hardness on the order of 15 Shore 00. Surprisingly, it was found that gel with a Shore hardness on the order of 15 Shore 00 is especially well suited for sealing the patient interface airtight at elevated ventilation pressure in the contact zone with the underside of the nares in a way that provides sufficient support and at the same time is comfortable for the patient.

Figure 22:
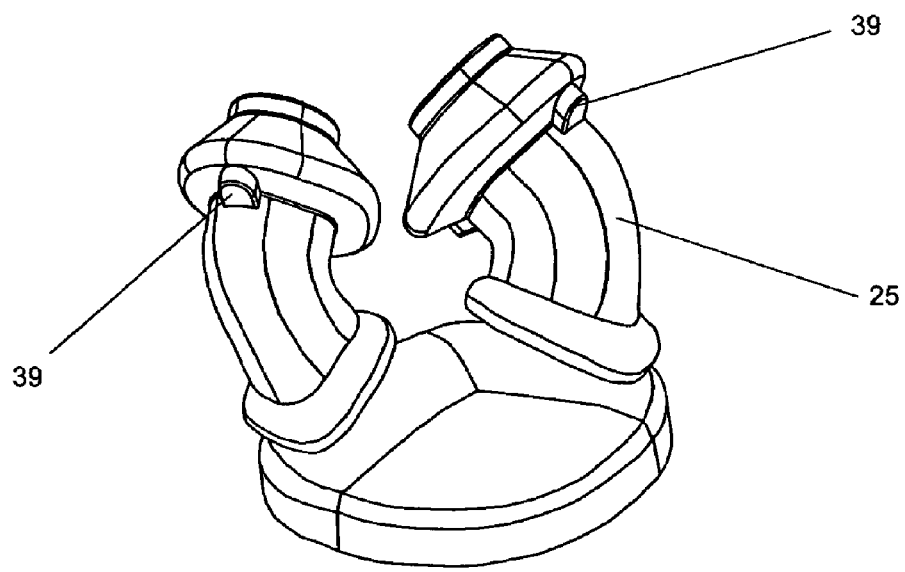
FIG. 22 shows a nasal pillow with two membrane openings.
Figure 23:
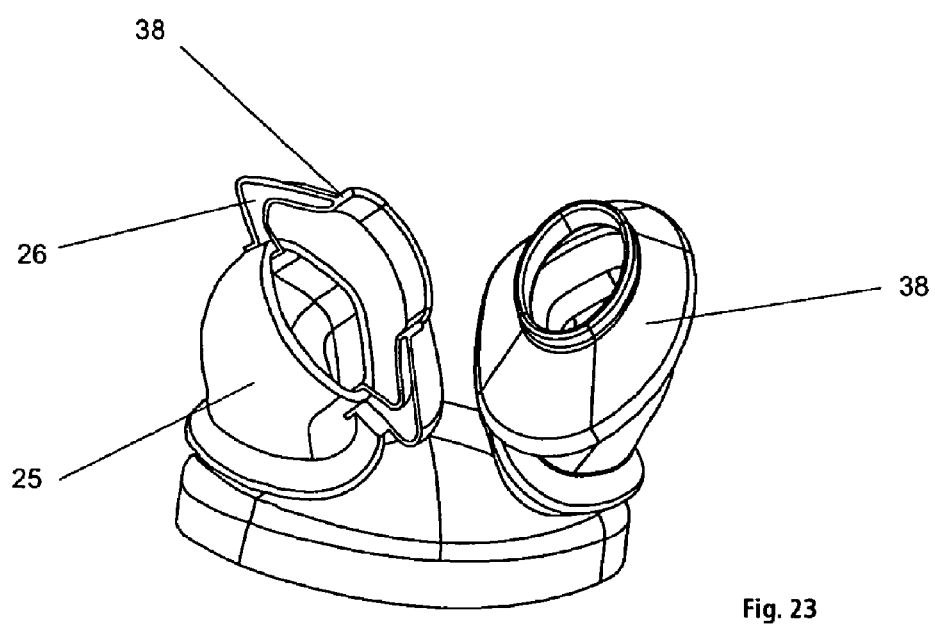
FIG. 23 shows a modification of FIG. 23.

The filling can be carried out in a variety of ways. In a first variant, the nasal pillows can be realized as a single piece, and the gel filling 26 can be injected through a membrane 39 in the covering that is located on the side of the nasal pillows that faces away from the patient. Each nasal pillow has two membrane openings 39, which serve the purpose of filling and simultaneous venting during filling. This is illustrated in FIG. 22. In another variant (FIG. 23), the body 25 of the nasal pillow and the two nasal pillow cushions 38 are produced separately, and the nasal pillow cushions 38 are filled with the gel 26 before it is joined with the body 25 by adhesive bonding.

The nasal pillow cushions 38 and the body 25 of the nasal pillow are secured against torsion by a tongue-and-groove joint to prevent incorrect assembly of the nasal pillows. The wall shape and thickness of the pockets to be filled with gel can be variable. The gel filling is preferably located in a region of the nasal pillows that rests against the underside of the nares and also extends at least partially into the region of the nasal pillows, which are inserted in the nose. In addition, the silicone covering is 10-50% thinner in the area of the gel fillings than the rest of the wall and preferably 20-40% thinner in order to guarantee better adaptation to the patient.

Other variants of embodiments with support on the bridge of the nose or on the side of the nose allow the patient a free field of vision. For one thing, the nose support can be accomplished by means of small, commercially available spectacle bridges or by a relatively large-area gel pad, which is mounted on the nose support and preferably is suitable for patients who are very sensitive to pressure. The mount of the nose bridge support is connected by a snap-in mechanism with the guide part of the forehead support, so that optimum adjustment is guaranteed. The variants of embodiments shown in FIGS. 22 and 23 can be realized both as a nose support without a forehead support and as a nose support with a forehead support.

By varying the silicone Shore hardness, e.g., the attachment region in the gel variant, more precisely, the double shot bubble and the actual connection shoulder, could be harder than in the standard silicone variant injected in one piece. This would not be noticed or would hardly be noticed (not disturbing) in a comparison of gel with silicone and would be helpful during mounting.

It is also possible to produce the gel forehead pad covering by a type of gas injection technique. In other words, the forehead plate is inserted in a production mold, and silicone is injected through a borehole within the forehead plate (plastic plate that serves as a locking element of the forehead pad) in such a way that the silicone is deposited only on the outer covering of the bell-shaped forehead pad (material is deposited as a skin on the inside of the mold wall) (wall thicknesses of 0.5-1.0 mm). This technique allows fabrication of the covering without a mold core (steel core that forms the inner region of the covering in a conventional mold).

The invention claimed is:

1. A method of producing a sealed covering for a patient interface for resting on an outer surface of a patient's body, wherein a covering blank is sealed by a stopper and a permanent connection between the covering blank and the stopper is produced by the use of a joining element, and wherein the sealed covering is produced from a uniform material.

2. The method of claim 1, wherein the uniform material is silicone.

3. The method of claim 1, wherein the joining element is liquid silicone.

4. The method of claim 1, wherein the joining element is activated by action of energy.

5. A method of producing a patient interface for resting on an outer surface of a patient's body and containing a gel filling, wherein a gel covering formed from a flexible material has a cavity at least in some areas thereof and has at least one dedicated opening which is sealed with a stopper and through which the cavity is filled with gel in liquid form, which thereafter cures in the gel covering, and wherein adhesive is used to join the gel covering and the stopper.

6. A method of producing a patient interface for resting on an outer surface of a patient's body and containing a gel filling, wherein a gel covering formed from a flexible material has a cavity at least in some areas thereof and has at least one dedicated opening which is sealed by the covering's own elasticity and through which the cavity is filled with gel in liquid form, which thereafter cures in the gel covering.

7. A method of producing a patient interface for resting on an outer surface of a patient's body and containing a gel filling, wherein a gel covering formed from a flexible material has a cavity at least in some areas thereof and has at least one dedicated opening which is sealed by cured gel and through which the cavity is filled with gel in liquid form, which thereafter cures in the gel covering.

8. A method of producing a patient interface for resting on an outer surface of a patient's body and containing a silicone gel filling, wherein a gel covering formed from a flexible material has a cavity at least in some areas thereof and has at least one dedicated opening through which the cavity is filled with silicone gel in liquid form, which thereafter cures in the gel covering, the silicone gel having a silicone oil fraction of less than 20%.

9. The method of claim 8, wherein the silicone gel contains no silicone oil.

10. The method of claim 8, wherein the at least one dedicated opening in the gel covering is sealed with a stopper.

11. The method of claim 8, wherein the at least one dedicated opening is produced in the gel covering by puncturing the gel covering with an injection device and the gel covering is filled with liquid gel by the injection device.

12. The method of claim 8, wherein the at least one dedicated opening in the gel covering is sealed by cured gel.

13. A method of producing a patient interface for resting on an outer surface of a patient's body and containing a gel filling, wherein a gel covering formed from a flexible material has a cavity at least in some areas thereof and has at least one dedicated opening through which the cavity is filled with gel in liquid form, which thereafter cures in the gel covering, the cured gel having a hardness, at least in some areas, of from about 10 Shore 00 to about 30 Shore 00.

14. The method of claim 13, wherein the cured gel has a hardness, at least in some areas, of from about 12 Shore 00 to about 20 Shore 00.

15. The method of claim 13, wherein the at least one dedicated opening in the gel covering is sealed with a stopper.

16. The method of claim 13, wherein the at least one dedicated opening is produced in the gel covering by puncturing the gel covering with an injection device and the gel covering is filled with liquid gel by the injection device.

17. A method of producing a patient interface for resting on an outer surface of a patient's body and containing a gel filling, wherein a gel covering formed from a flexible material has a wall thickness, at least in some areas, of about 0.5 mm and has a cavity at least in some areas thereof and has at least one dedicated opening through which the cavity is filled with gel in liquid form, which thereafter cures in the gel covering.

18. A method of producing a patient interface for resting on an outer surface of a patient's body and containing a gel filling, wherein the patient interface is for use with a nasal pillow and wherein a gel covering formed from a flexible material has a cavity at least in some areas thereof and has at least one dedicated opening through which the cavity is filled with gel in liquid form, which thereafter cures in the gel covering.

19. A method of producing a patient interface for resting on an outer surface of a patient's body and containing a gel filling, wherein the patient interface is for use with a face mask and wherein a gel covering formed from a flexible material has a cavity at least in some areas thereof and has at least one dedicated opening through which the cavity is filled with gel in liquid form, which thereafter cures in the gel covering.

20. A method of producing a patient interface for resting on an outer surface of a patient's body and containing a gel filling, wherein the patient interface is for use with an oral mask and wherein a gel covering formed from a flexible material has a cavity at least in some areas thereof and has at least one dedicated opening through which the cavity is filled with gel in liquid form, which thereafter cures in the gel covering.

* * * * *